(12) United States Patent
Magvasi

(10) Patent No.: US 6,372,263 B1
(45) Date of Patent: Apr. 16, 2002

(54) ACTIVE SUBSTANCE AND COMPOSITION INHIBITING TUMOROUS PROLIFERATION IN ECTODERM DERIVED TISSUES

(76) Inventor: Gyula Magvasi, Bécsi út 34., H-1037, Budapest (HU)

( * ) Notice: Subject to any disclaimer, the term of this patent is extended or adjusted under 35 U.S.C. 154(b) by 0 days.

(21) Appl. No.: 09/381,894
(22) PCT Filed: Mar. 24, 1998
(86) PCT No.: PCT/HU98/00031
  § 371 Date: Sep. 23, 1999
  § 102(e) Date: Sep. 23, 1999
(87) PCT Pub. No.: WO98/43996
  PCT Pub. Date: Oct. 8, 1998

(30) Foreign Application Priority Data

Mar. 28, 1997 (HU) ............................................. 9700673
May 9, 1997 (HU) ............................................. 9701165

(51) Int. Cl.[7] .............................................. A61K 35/54
(52) U.S. Cl. ....................................... 424/581; 424/582
(58) Field of Search ................................. 424/581, 582

(56) References Cited

U.S. PATENT DOCUMENTS 5,962,410 A 10/1999 Jaynes et al. ................. 514/12

FOREIGN PATENT DOCUMENTS

WO  WO 98/55136  12/1998

OTHER PUBLICATIONS

U.S. application No. 08/869,153, McCann et al., filed Jun. 1997.

Tang, D. et al., "Target to Apoptosis: A Hopeful Weapon for Prostate Cancer," *The Prostate*, vol. 32, pp. 284–293 (1997).

Yu, W. et al., "A hypothalamic follicle–stimulating hormone–releasing decapeptide in the rat," *Proc. Natl. Acad. Sci USA*, vol. 94, pp. 9499–9503 (1997).

Mezö, I. et al., "Synthesis of Gonadotropin–Releasing Hormone III Analogs. Structure–Antitumor Activity Relationships," *J. Med. Chem.* vol. 40, pp. 3353–3358 (1997).

*Primary Examiner*—Jean C. Witz
(74) *Attorney, Agent, or Firm*—Herbert Dubno; Jonathan Myers

(57) ABSTRACT

The invention relates to an active substance inhibiting tumorous proliferation in ectoderm derived tissues and to a composition containing such substance. A process for producing the above active substance comprises the following steps:

fertilized ovum of human beings or sea water fishes or fresh water fishes is subjected to cell wall destruction preferably 24 hours, more preferably 14–16 hours after fertilization, then the material is ultracentrifuged, the supernatant is separated, the sediment is homogenized, then ultracentrifuged several times, and each time the supernatant and the sediment are separated, thereafter all supernatant fractions are combined and centrifuged preferably at 8,000–15,000 rpm, the supernatant obtained is separated and diluted preferably with physiological solution, preferably in 1:2 ratio by weight, then the active substance is separated from contaminants, preferably the obtained material is subjected to a series of gel filtration at least twice, then the filtered substance is lyophilized.

14 Claims, No Drawings

ACTIVE SUBSTANCE AND COMPOSITION INHIBITING TUMOROUS PROLIFERATION IN ECTODERM DERIVED TISSUES

The invention relates to an active substance and composition inhibiting tumorous proliferation in ectoderm derived tissues and to the process for producing thereof.

One of the most serious illness in the 20th century is cancer. Many experimental works have the aim to discover the reason of the formation of tumorous tissue proliferation.

The formation of tumorous cells and the properties of these cells are discussed in the following publications: Cancer Res. 47., p. 1473, 1987; European Journal of Cancer 15., p. 585, 1979; Science 197., p. 893, 1977; Int. Rev. Exp. Pathol, 16., p. 207, 1976.

Several drugs and compositions are known which inhibit the tumorous proliferation. The active ingredient of the composition is either natural or synthetic. Thus, for example the tumor inhibiting effect of natural active substances isolated from plants is discussed in the following papers: Ukrain. J. Cell. Biochem., 1987., Suppl. 11A: 53; J. Tumor Marker Oncol., 1988, 3., p. 463–465.

In the course of our research work we suggested that the reason of the cell proliferation in ectoderm derived differentiated tissues could be that because of the liberation of the previously suppressed primordial reproduction code the new cells start an endless reproduction. The multiplying new cells form an aggregate (tumor tissue) and by means of their metalloprotease enzyme they lyse the surrounding tissues. Growing in such a diffuse way they advance into their environment, and after causing erosion of vessels they get into the lymphatic system and blood circulation. The detached cells can induce neoplasm in places far from the primary tumor. This cell proliferation schema corresponds to the cell reproduction according to the endless cell reproduction code in the early stage of phylogenesis.

In primordial times to the formation of an organic structure instead of a cell aggregate the suppression of the endless cell reproduction code was necessary and the building of a code into the cell which would ensure the formation and the function of the given organization.

It is known that in animals including humanoids, the DNA contains the code system of formation and function of organizations.

In the coarse of our studies we have discovered that the basic event which causes the malignous transformation of the cell functioning previously differentiatedly, takes place on DNA level.

Our aim was to provide an active substance containing those codes which are capable to inhibit the endless and speedy cell reproduction. We have found that the substance containing this genetic code, probably connected to RNA, can be isolated from fertilized ovum.

It is known from WO-A-96/39428, WO-A-91/07435, WO-A-89/09606, that it is possible to produce proteins from Rana pipiens fertilized eggs which have antitumor effect. This active substance has a different composition, different molecular weight (preferable 4000–6000 dalton) and effect, because of the different starting material.

For the preparation of the active substance according to the invention human or animal derived fertilized ovum, preferably the fertilized ovum of a fish is used as starting material. The fertilized ovum of the following fish species can advantageously be applied: *Cyprinus carpio, Tinca tinca, Gobio gobio, Gobio uranoscopus, Barbus barbus, Barbus meridionalis petenyii, Hypophtalmichthys molitrix, Aristichtys nobilis, Carassius carassius, Carassius auratus gibelio, Leuciscus sonffia agassizi, Chondrostoma nasus, Pseudorasbora parva, Leuciscus idus, Cienopharyngodon idella, Leuciscus cephalus, Scardinius erythrophthalmus, Leuciscus leuciscus, Leuciscus virgo, Rutilus rutilus, Phoxinus phoxinus, Phoxinus percnurus, Leucaspius delineatus, Rhodeus sericeus amarus, Pelecus cultratus, Aspius aspius, Alburnus mento, Alburnus alburnus, Alburnoides bipunciatus, Vimba vimba, Blicca bjoerkna, Abramis brama, Abramis ballerus, Abramis sapa, Carassius auratus.*

In case when the fertilized ovum of a sea water fish or fresh water fish is used as starting material the fertilization is performed artificially and the embryonic development is interrupted at a stage where the endless reproduction stops and differentiated development starts. Therefore the fertilization is performed for 24 hours at most, preferably for 14–16 hours. The fertilized ovum prepared in this way is worked up according to the invention. The fertilization is performed preferable at 12–14° C. Thus, the subject of the present invention is an active substance inhibiting tumorous proliferation appearing in ectoderm derived tissueswhich is derivedfrom fertilezed ovum of human beings or sea water fishes or fresh water fishes, as well as a composition containing such substance. The subject of the invention the process for producing the active substance. The process is comprising the following steps: the fertilized ovum of human beings or sea water fishes or fresh water fishes is subjected to cell wall destruction with stirring 24 hours at most, preferably 14–16 hours after fertilization, then the mixture is ultracentrifuged, the supernatant is separated, the sediment is homogenized and ultracentrifuged several times in the coarse of which the supernatant and the sediment are separated, then all the supernatants are combined and centrifuged preferably at 8,000–15,000 rpm, the supernatant obtained is separated and diluted with physiological saline solution, preferably in 1:2 ratio by weight, the mixture is filtered at least twice through gel filters, then the filtered liquid is lyophilized. The subject of the invention is also the process for producing the composition which is containing the active substance. According to this process the active substance is mixed with additives or optionally is diluted with a diluent, preferably with physiological saline solution or dextrose solution or sterile distilled water, preferably in 1:2 ratio by weight. The fertilized ovum subjected to cell wall destruction can be stored in a deep-freezer preferably at −70° C. until final workup. Before use the frozen material is allowed to thaw in a water bath of 20–25° C. for 2–3 hours. The fertilized ovum subjected to cell wall destruction is ultracentrifuged at 25,000–30,000 rpm. Then the supernatant containing RNA is separated from the sediment consisting of mainly high molecular weight proteins and carbohydrates.

The sediment is ultracentrifuged again to separate the supernatant more properly from the fraction consisting of high molecular weight protein and carbohydrates. The combined supernatant containing the active substance is repeatedly centrifuged in order to effect a proper separation, then the supernatant obtained in this way is subjected to gel filtration for several times to remove proteins and bacteria.

The active substance prepared can be lyophilized or mixed with physiological solutions to form composition. In the composition the ratio of the active substance and the physiological solution can be optional, but preferably we prepare solutions in which the ratio of the active substance and the additives is 1:2 by weight.

The lyophilized active substance can be stored for unlimited time, the composition prepared by dilution with physiological saline solution or dextrose solution can be stored at −15° C. for 4 years.

We presume that with the supernatant of the fertilized ovum we separate the RNA from the carbohydrates and the high molecular weight proteins.

As tumor inhibiting agent the composition is to be administered intravenously in form of a cure. To a human patient of 70 kg body weight 1.5 ml of active substance is administered after dilution to 10 ml of volume, preferably with physiologic saline solution.

The treatment is performed according to the so called Besredka method. Before starting the cure 0.1 ml solution containing the active substance is diluted to 10 ml with physiological saline solution and administered to the patient. If sensitivity is experienced, the so called anaphylactic shock develops, the active substance content is increased gradually to 1.5 ml volume. In our experiments we have not observed such a sensitivity.

One cure lasts for 14 days, and every day 1.5 ml of active substance diluted to 10 ml with physiological saline solution (counted for 70 kg of body weight) is administered intravenously. After that, for a further 14 days the same composition is administered every other day.

After half a year a control is performed and if the tumor inhibiting effect was not satisfactory, an additional 14 days cure is applied with daily intravenous administration.

The active substance and composition according to the invention as well as the process of their preparation is illustrated by the following examples.

EXAMPLE 1

Female and male subjects of fresh water carp, *Cyprinus carpio* are separated.

From the female subjects roe, from the male subjects milt are stripped. The roe and the milt are mixed in a bottle to perform artificial fertilization.

The fertilized ovum is allowed to stand for 14 hours at 14° C. Then it is homogenized with sodium citrate buffer solution, and the mixture is stirred for 10 minutes to destroy the cell wall. The material obtained is deep-frozen and kept at −70° C. until workup. Before use the material is thawed in a water bath at 27° C. for 2 hours, and ultracentrifuged at 30,000 rpm for 4 hours.

The supernatant is separated, and the RNA-containing end product can be found in this fraction. The sediment is ultracentrifuged again at 35,000 rpm for 2 hours.

The supernatant is separated and all the supernatant fractions are combined, centrifuged at 10,000 rpm for 1 hour, then the supernatant is separated, and one part by weight of supernatant is mixed with 2 parts by weight of physiological saline solution.

The product is filtered in several stages through gel filters of different pore size. The pore diameter of the gel filters are 8μ, 0.8μ, 0.45μ, 0.22μ respectively. Then the above series of filtration is repeated, the filtered material is diluted with sterile water to threefold of its original volume, and the bacterium level is determined.

A sample of the prepared product is streaked on bloody agar culture medium and incubated for 24 hours. After 24 hours there was no bacterium culture present, so we stated that the product was free of bacterium.

The composition was subjected to endotoxin test. The determined endotoxin value was 3U/ml. The endotoxin level of the composition is suitable.

The composition is filled into ampules. The formulated composition can be stored at −18° C. for two years.

EXAMPLE 2

The nondiluted active substance according to Example 1 is subjected to HPLC examination. The result shows that the peaks characterizing for the active substance are between 4,000 and 10,000 Dalton. The active substance can be identified by these peaks.

EXAMPLE 3

The procedure according to Example 1 is repeated, but *Aristichtys nobilis* is used as starting subject. Then the process described in Example 1 is followed with the exception that after gel filtrations the material obtained is lyophilized. The lyophilized substance is stored in ampules.

EXAMPLE 4

Pharmacological Test

The effect of the active material according to Example 1 was tested in vitro using MCF-7 human lung carcinoma tissue. The MCF-7 carcinoma tissue was obtained form the Institute of Oncology, Budapest.

The cell number of the carcinoma tissue is 7×10−4 cell/ml. The cultivation is carried out on Greiner plates in RPMI culture medium supplied with 2% by weight of bovine serum. In Experiment 1 300 ml of active substance according to Example 1 is added to 200 ml of medium, in Experiment 2 150 ml of active substance was added to 850 ml of medium and in Experiment 3 30 ml of active substance is added to 970 ml of medium. In the control experiment instead of active substance distilled water is added to the culture medium. The experiments were performed in three parallel repetition.

Observations take place after 24, 48 and 72 hours. The number of cells as well as the % of the viable cells are determined by means of methylene blue staining method.

The results of the test are shown in the following table:

|  | After 24 hours | | After 48 hours | | After 72 hours | |
| --- | --- | --- | --- | --- | --- | --- |
| Experiment | Number of Cells ×105/ml | Viability % | Number of Cells ×105/ml | Viability % | Number of Cells ×105/ml | Viability % |
| Control | 0,81 ± 0,13 | 99 ± 2 | 2,90 ± 0,62 | 100 ± 0 | 4,27 ± 1,03 | 96 ± 7 |
| Exp. 1 | 0,65 ± 0,02 | 97 ± 3 | 1,33 ± 0,49 | 95 ± 5 | 0,80 ± 0,17 | 47 ± 36 |
| Exp. 2 | 0,89 ± 0,05 | 93 ± 3 | 1,73 ± 0,55 | 95 ± 5 | 1,60 ± 0,70 | 65 ± 13 |
| Exp. 3 | 0,91 ± 0,20 | 97 ± 1 | 2,87 ± 0,83 | 93 ± 6 | 1,67 ± 0,35 | 52 ± 4 |

It can be seen from the results that the composition according to the invention strongly inhibits the proliferation of MCF-7 tumorous tissue already in the lowest examined concentration. According to the examination the maximum of the inhibiting activity is reached after 72 hours. The culture is subjected to morphological examination, i.e. one control and one treated culture are examined. In the control experiment distilled water is added to the culture medium instead of active substance. Both the control and the treated culture show mitotic and apoptic activity. According to our experience in Experiments 1–3 in the period of 48–72 hours after the treatment with the active substance the measure of apoptosis exceeds that of mitosis.

I claim:

1. An active substance which contains RNA and which inhibits tumorous proliferation in ectodermal tissues, said active substance extracted from a fertilized ovum of a sea water fish or a fresh water fish.

2. A composition for inhibiting tumorous proliferation in ectodermal tissues which comprises a therapeutically effective amount of the active substance defined in claim 1 in combination with a pharmaceutically acceptable additive.

3. The composition defined in claim 2 wherein the pharmaceutically acceptable additive is a diluent.

4. A process for preparing an active substance which contains RNA and which inhibits tumorous proliferation in ectodermal tissues, said active substance extracted from a fertilized ovum of a sea water fish or a fresh water fish, which comprises the following steps:

(a) subjecting a fertilized ovum of a sea water fish or a fresh water fish to cell wall destruction after fertilization to obtain a material;

(b) ultracentrifuging the material prepared according to step (a) to form a sediment containing proteins and carbohydrates and a supernatant fraction containing RNA and recovering the supernatant fraction containing RNA;

(c) homogenizing the sediment and subjecting the homogenized sediment to additional ultracentrifuging to obtain additional supernatant fractions containing RNA;

(d) combining the supernatant fractions obtained according to steps (b) and (c) and centrifuging the combined supernatant fractions at 8,000 to 15,000 rpm to obtain a final supernatant containing RNA;

(e) separating the final supernatant containing RNA and diluting the final supernatant with a physiological solution to obtain the active substance which contains RNA and which inhibits tumorous proliferation;

(f) separating the active substance which contains RNA and which inhibits tumorous proliferation from contaminants; and (g) gel-filtering at least twice, the active substance which contains RNA separated from contaminants according to step (f) to obtain a filtered active substance which contains RNA; and (h) lyophilizing the filtered active substance which contains RNA.

5. The process for preparing an active substance which contains RNA and which inhibits tumorous proliferation defined in claim 4 wherein according to step (a) the cell wall destruction takes place 24 hours after fertilization.

6. The process for preparing an active substance which contains RNA and which inhibits tumorous proliferation defined in claim 4 wherein according to step (a) the cell wall destruction takes place 14 to 16 hours after fertilization.

7. The process for preparing an active substance which contains RNA and which inhibits tumorous proliferation defined in claim 4 wherein according to step (e) the weight ratio of the supernatant obtained and the physiological solution used to dilute the final supernatant is 1:2.

8. The process for preparing an active substance which contains RNA and which inhibits tumorous proliferation defined in claim 4 wherein according to step (b) the fertilized ovum subjected to cell wall destruction is ultracentrifuged at 25,000 to 30,000 rpm.

9. The process for preparing an active substance which contains RNA and which inhibits tumorous proliferation defined in claim 4 wherein according to step (g) the active substance is filtered through gel filters of $8\mu$, $0.8\mu$, $0.45\mu$, and $0.22\mu$ pore diameters.

10. The active substance which contains RNA and which inhibits tumorous proliferation in ectodermal tissues, said active substance extracted from a fertilized ovum of a sea water fish or a fresh water fish prepared by the process defined in claim 4.

11. A process for producing a composition for inhibiting tumorous proliferation in ectodermal tissues which comprises the step of diluting the therapeutically effective amount of the active substance which contains RNA and which inhibits tumorous proliferation in ectodermal tissues, said active substance extracted from a fertilized ovum of a sea water fish or a fresh water fish prepared according to claim 4 with a diluent.

12. The process for producing a composition for inhibiting tumorous proliferation defined in claim 11 wherein the diluent is physiological saline solution, a dextrose solution, or sterile distilled water and the weight ratio of the active substance and the diluent is 1:2.

13. The active substance which contains RNA and which inhibits tumorous proliferation defined in claim 1 wherein the fertilized ovum is extracted from a fresh water fish.

14. The active substance which contains RNA and which inhibits tumorous proliferation defined in claim 13 wherein the fresh water fish is a fresh water carp.

\* \* \* \* \*